United States Patent
Lang et al.

(10) Patent No.: US 6,660,035 B1
(45) Date of Patent: Dec. 9, 2003

(54) ACCOMMODATING INTRAOCULAR LENS WITH SUSPENSION STRUCTURE

(75) Inventors: Alan J. Lang, Long Beach, CA (US); Edward R. Zaleski, Santa Ana, CA (US); Marcia S. Yaross, Glendora, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 158 days.

(21) Appl. No.: 09/631,223

(22) Filed: Aug. 2, 2000

(51) Int. Cl.$^7$ .................................................. A61F 2/16
(52) U.S. Cl. ...................................... 623/6.37; 623/6.49
(58) Field of Search ............................... 623/6.37–6.39, 623/6.22, 6.11, 6.32, 6.34, 6.43, 6.44, 6.46, 6.49, FOR 105

(56) References Cited

U.S. PATENT DOCUMENTS

| | | | |
|---|---|---|---|
| 1,483,509 | A | 2/1924 | Bugbee |
| 2,129,305 | A | 9/1938 | Feinbloom |
| 2,274,142 | A | 2/1942 | Houchin |
| 2,405,989 | A | 6/1946 | Beach |
| 2,511,517 | A | 6/1950 | Spiegel |
| 3,031,927 | A | 5/1962 | Wesley |
| 3,034,403 | A | 5/1962 | Neefe |

(List continued on next page.)

FOREIGN PATENT DOCUMENTS

| | | |
|---|---|---|
| AU | 3225789 | 10/1989 |
| DE | 2702117 | 7/1978 |
| DE | 3246306 | 6/1984 |
| EP | 0246216 | 11/1987 |
| EP | 0329981 | 8/1989 |
| EP | 0337390 | 10/1989 |

(List continued on next page.)

OTHER PUBLICATIONS

Menezo et al. J Cataract Refract. Surg 24, Aug. 1998 (Published in U.S.), pp. 1039–1049.
Fechner et al. J Cataract Refract. Surg 24, Jan. 1998 (Published in U.S.), pp. 48–56.
AMO Specs, Model AC–218, 1992 (Published in U.S.), 5 pages.
Chiron Vision, Nuvita MA20, 1997 (Chiron Vision Corp. 1997), 6 pages.
Video Tape "New Elliptical Acco IOL for Cataract Surgery" Shown at ASCRS Symposium on Apr. 10, 1999.
Partial Program Re: ASCRS Symposium, Showing Video Tape Shown Between Apr. 10–14, 1999, 2 pages.
Patent application Ser. # 09/656,661 filed Sep. 7, 2000.
Patent application Ser. # 09/721,072 filed Nov. 22, 2000.
Patent application Ser. # 09/657,325 filed Sep. 7, 2000.
Patent application Ser. # 09/657,251 filed Sep. 7, 2000.
Patent application Ser. # 09/390,380 filed Sep. 3, 1999.
Patent application Ser. # 09/565,036 filed May 3, 2000.
Patent application Ser. # 09/522,326 filed Mar. 9, 2000.
Patent applciation Ser. # 09/532,910 filed Mar. 22, 2000.
Patent application Ser. # 09/795,929 filed Feb. 28, 2001.
Patent application Ser. # 09/822,040 filed Mar. 30, 2001.

*Primary Examiner*—David H. Willse
(74) *Attorney, Agent, or Firm*—Peter Jon Gluck

(57) ABSTRACT

An intraocular lens includes an optic for focusing light and a movement assembly coupled to the optic. The movement assembly is adapted to cooperate with the eye to effect accommodating movement of the optic. The movement assembly includes a plurality of movement members and a suspension structure. The movement members are coupled to a periphery of the optic. The suspension structure is coupled to the movement members and is adapted to be in contact with a peripheral region of a capsular bag of an eye. The movement members are adapted to convert radial movement of the suspension structure caused by movement of the capsular bag to axial movement of the optic. The movement members are also adapted to amplify the radial movement of the suspension structure so that the optic moves axially a greater distance than the distance moved radially by the suspension structure.

11 Claims, 5 Drawing Sheets

U.S. PATENT DOCUMENTS

| | | |
|---|---|---|
| RE25,286 E | 11/1962 | Decarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | DeCarle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | DeCarle |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,968 A | 6/1990 | Caldwell, et al. |
| 4,938,583 A | 7/1990 | Miller |
| 4,955,902 A | 9/1990 | Kelman |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,443,506 A | 8/1995 | Garabet |
| 5,476,514 A | 12/1995 | Cumming |
| 5,480,428 A | 1/1996 | Fedorov et al. |
| 5,496,366 A | 3/1996 | Cumming |
| 5,521,656 A | 5/1996 | Portney |
| 5,562,731 A | 10/1996 | Cumming |
| 5,578,081 A | 11/1996 | McDonald |
| 5,607,472 A | 3/1997 | Thompson |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,843,188 A | 12/1998 | McDonald |
| 6,013,101 A * | 1/2000 | Israel ........................ 623/6.43 |
| 6,096,078 A | 8/2000 | McDonald |
| 6,176,878 B1 | 1/2001 | Gwon et al. |
| 6,217,612 B1 | 4/2001 | Woods |
| 6,231,603 B1 | 5/2001 | Lang et al. |

FOREIGN PATENT DOCUMENTS

| | | |
|---|---|---|
| EP | 0342895 | 11/1989 |
| EP | 0351471 | 1/1990 |
| EP | 0356050 | 2/1990 |
| EP | 0566170 | 10/1993 |
| EP | 0691109 | 1/1996 |
| EP | 9743984 | 11/1997 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| GB | 939016 | 1/1996 |
| WO | 8603961 | 7/1986 |

| | | | | | | |
|---|---|---|---|---|---|---|
| WO | 8707496 | 12/1987 | WO | 9625126 | 8/1996 | |
| WO | 8902251 | 3/1989 | WO | wo99/03427 | * 1/1999 | ........ 623/FOR 105 |
| WO | 8911672 | 11/1989 | WO | 00/35379 | 6/2000 | |
| WO | 9416648 | 8/1994 | WO | 0134067 | 5/2001 | |
| WO | 9503783 | 2/1995 | | | | |
| WO | 9615734 | 5/1996 | | | | |

* cited by examiner

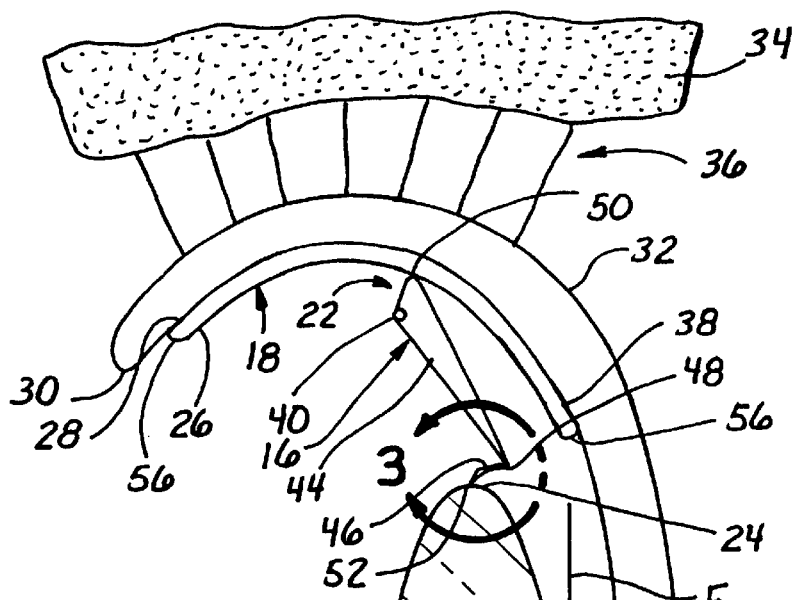
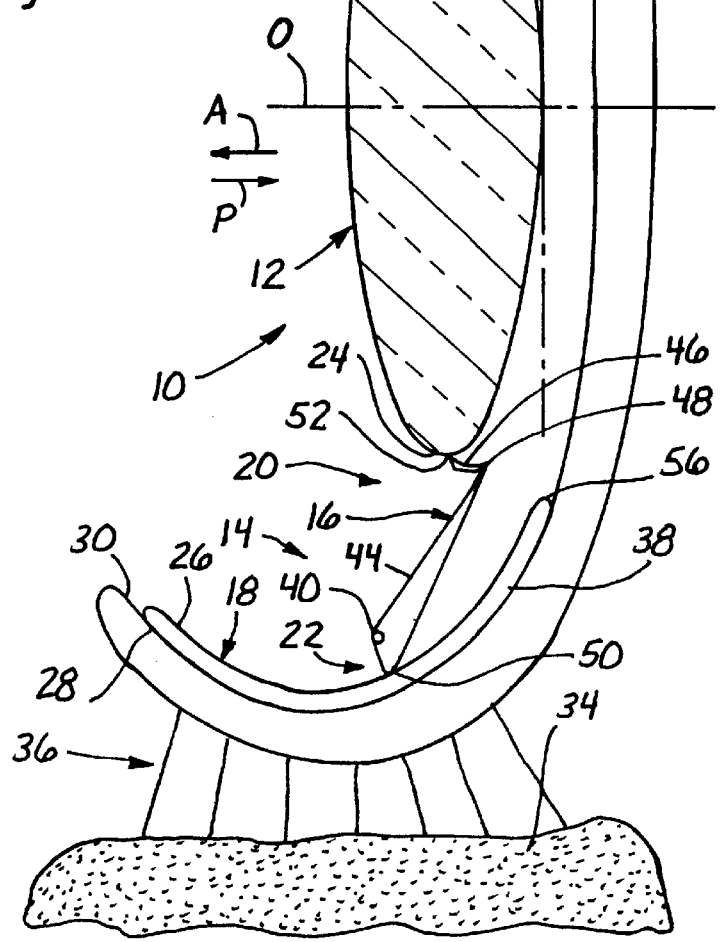
Fig. 1

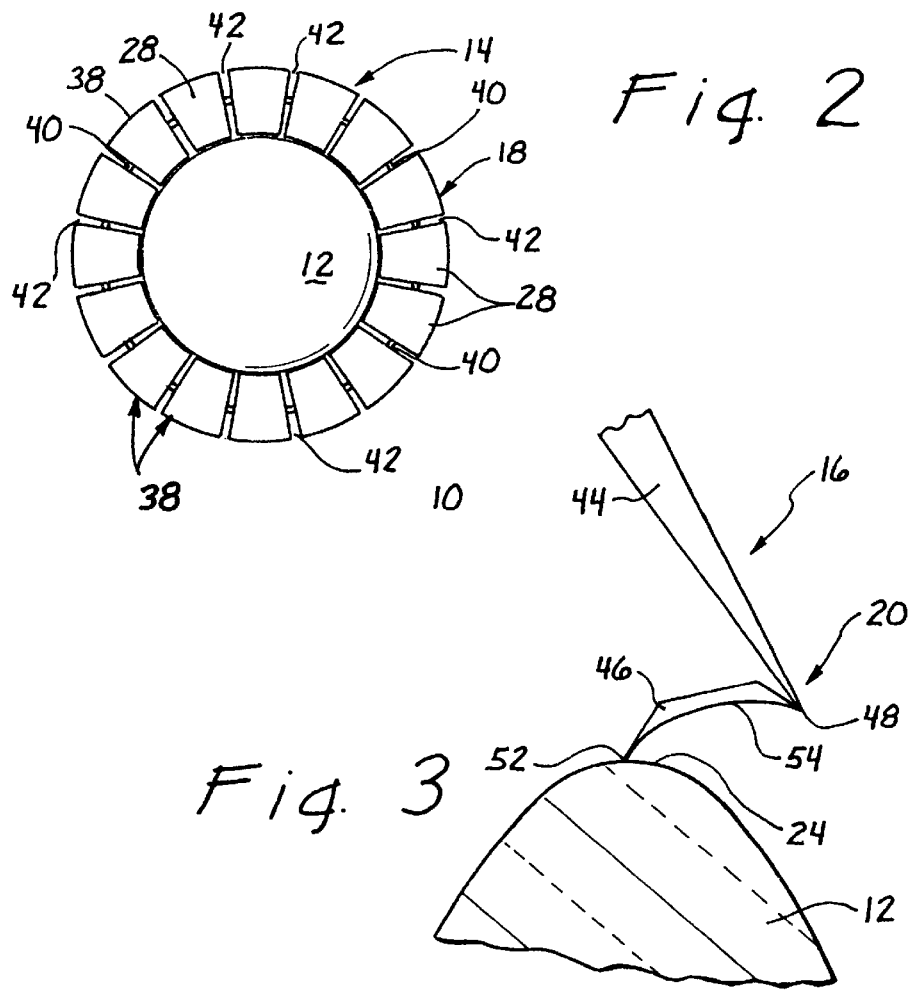
Fig. 2
Fig. 3
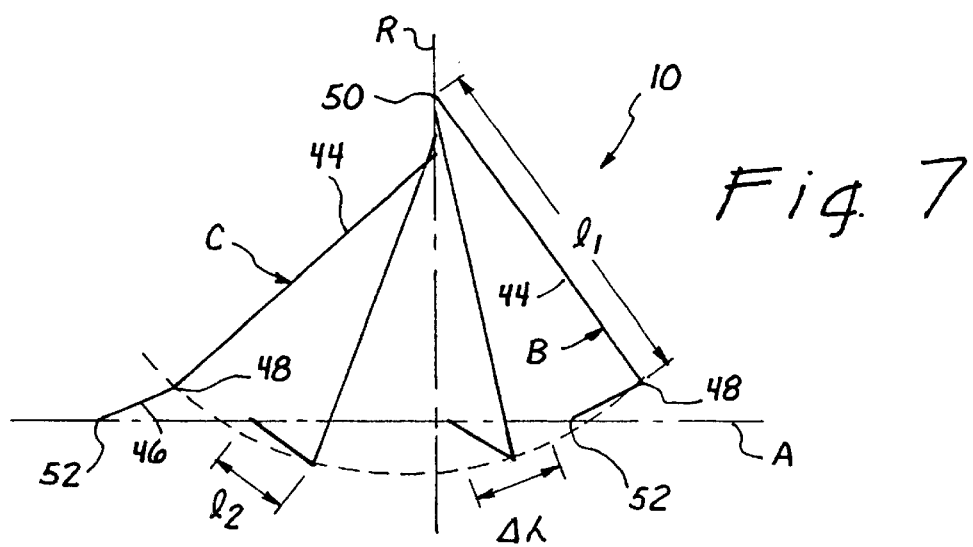
Fig. 7

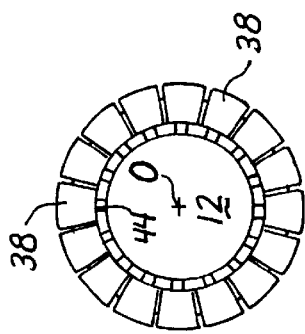
Fig. 6C2
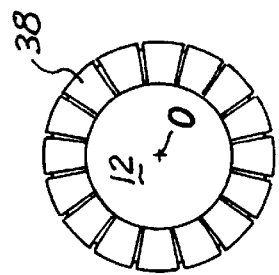
Fig. 6B2
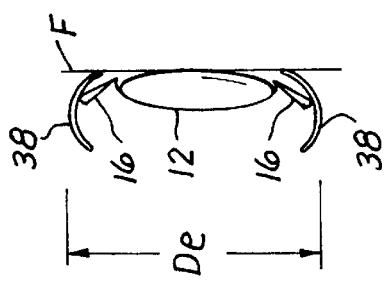
Fig. 6C1
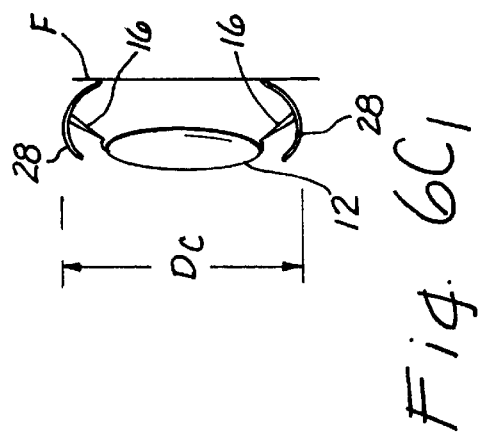
Fig. 6B1
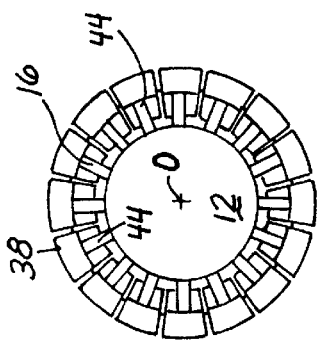
Fig. 6C3
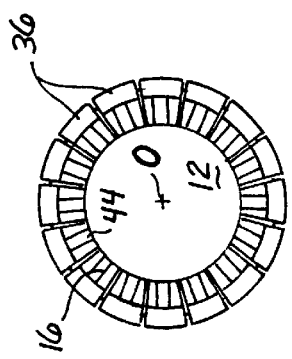
Fig. 6B3

ACCOMMODATING INTRAOCULAR LENS WITH SUSPENSION STRUCTURE

BACKGROUND OF THE INVENTION

The present invention relates to intraocular lenses (IOLs). More particularly, the present invention relates to IOLs that provide accommodating movement in the eye.

The human visual system includes the eyes, the extraocular muscles which control eye position within the eye socket, the optic and other nerves that connect the eyes to the brain, and particular areas of the brain that are in neural communication with the eyes. The visual system is particularly well adapted for the rapid and precise extraction of spatial information from a field of view which is accomplished by analyzing the continuously changing patterns of radiant flux impinging upon the surfaces of the eyes.

Image formation is greatly complicated by the movement of the eyes within the head, as well as by the movement of both eyes and the head relative to the external sea of radiant energy. Visual input is ordinarily sampled by discrete momentary pauses of the eyes called fixations, interrupted by very rapid ballistic motions known as saccades which bring the eye from one fixation position to the next. Smooth movements of the eyes can occur when an object having a predictable motion is available to be followed.

Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber. The crystalline lens is contained within a third chamber of the eye, the posterior chamber, which is positioned between the anterior and vitreous chambers.

The human eye is susceptible to a score or more of disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of the IOL, e.g., to become more convex to focus on near objects, or by moving the IOL along its optical axis. For example, a number of these approaches bias an IOL to be located in the most posterior position of the posterior chamber of the eye under rest conditions. When near focus is required, the ciliary muscle contracts, and the IOL moves forwardly, which is known as positive accommodation. In the absence of ciliary muscle contraction, the IOL is biased rearwardly to the most posterior position. While these approaches may provide limited accommodation, the posterior bias and the configuration of the IOL prevent sufficient forward axial movement required for full-range accommodation.

In view of the foregoing, it would be beneficial in the art to provide IOLs adapted for sufficient accommodation to reduce significantly or to overcome the effects of presbyopia.

SUMMARY OF THE INVENTION

The present invention provides new and enhanced intraocular lenses (IOLs). The present IOLs enhance accommodation of an optic. More specifically, the IOLs of the present invention enhance accommodation by converting radial movement of the capsular bag to axial movement of an optic. In addition, the present IOLs may also amplify such radial movement to effect a greater degree of positive accommodation for near vision.

According to one aspect of the present invention, an intraocular lens includes an optic and a movement assembly. The optic is adapted to focus light onto a retina of an eye. The movement assembly is adapted to cooperate with the eye to effect accommodating movement of the optic along an optical axis thereof. The movement assembly includes at least one, and preferably a plurality of, movement members and a suspension structure. The movement members are coupled to a periphery of the optic. The suspension structure is coupled to the movement members and is adapted to be in contact with a peripheral region of a capsular bag of an eye. The movement members are adapted to convert radial movement of the suspension structure caused by movement of the capsular bag to axial movement of the optic.

One of the advantages of the present invention is that the movement members may be adapted to amplify the radial movement of the suspension structure. Accordingly, substantial positive accommodation for near vision is possible with a relatively small contraction of the capsular bag. For example, according to one preferred embodiment of the invention, the movement members are configured to increase or amplify radial movement of the suspension structure into axial movement of the optic by approximately 200%.

According to another aspect of the IOL of the present invention, the movement members are articulated. For example, each of the movement members may include a first segment and a second segment pivotally coupled together. A distal end of the first segment is pivotally coupled to the suspension structure, and a proximal end of the second segment is pivotally coupled to a periphery of the optic.

This articulated two-segment linkage arrangement of the movement members allows radial movement to be converted and amplified into axial movement. More specifically, radial forces directed inwardly during contraction of the capsular bag are carried by the first segment. These forces are then transferred to the second segment at a pivot disposed between the two segments. The first segment and, correspondingly, the optic are urged anteriorly. This motion is amplified as the capsular bag continues to contract as the pivot follows a curved path which is translated into substantially axial movement of the optic.

According to another aspect of the invention, the suspension structure may include a plurality of arcuate contact plates each coupled to a respective one of the movement members. The arcuate contact plates are configured to support the IOL within the capsular bag. One of the advantages of this embodiment of the present invention is that the IOL is vigorously held within the capsular bag. More specifically, the contact plates collectively have a relatively large contact surface which engages with and supports the capsular bag.

The relatively large surface area of the contact plates may also promote cellular and fibrous growth to this portion of the IOL, which further holds and retains the IOL within the capsular bag. Post-operative cellular and fibrous growth of the interior of the capsular bag to the contact plates is facilitated by the vigorous contact of the contact surface with the capsular bag.

In addition to promoting desired post-operative fibrous growth, the IOL of the present invention inhibits unwanted posterior capsule opacification (PCO) onto the optic. To do so, the movement assembly may include a plurality of sharp discontinuities between the contact plates and the optic. Accordingly, cellular growth from the capsular bag to the optic is inhibited.

According to another aspect of the IOL of the invention, the suspension structure may include a fulcrum ring coupled to the movement members, thereby interconnecting the movement members. The first segment of each movement member rotates about the fulcrum ring during accommodation.

Any and all of the features described herein and combinations of such features are included within the scope of the present invention provided that the features of any such combination are not mutually inconsistent.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

FIG. 1 is a cross sectional view of an intraocular lens (IOL) according to an exemplary embodiment of the present invention implanted in a capsular bag of a human eye.

FIG. 2 is a plan view of an IOL configured in accordance with the present invention, particularly illustrating the IOL from a posterior side.

FIG. 3 is an enlarged cross sectional view of an intraocular lens (IOL) of the invention, particularly illustrating an articulated movement member of the invention.

Figure 4A:
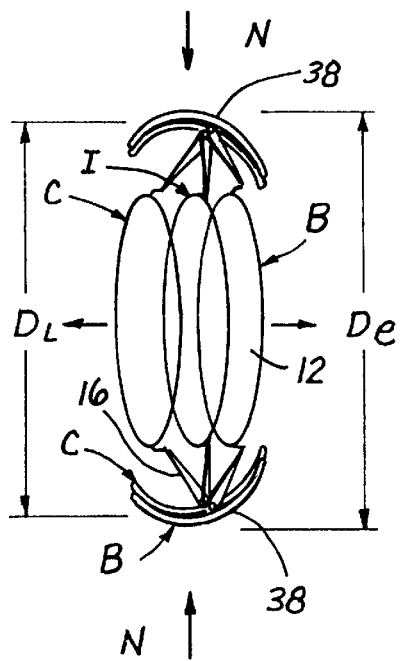
FIG. 4A is a schematic sectional view of an IOL of the invention illustrating various positions of accommodation of an optic.

FIG. $6B_1$ is a schematic sectional view of an IOL of the invention illustrating a most-rearward position of an optic of the IOL.

FIG. $6B_2$ is an on-axis elevational view of the IOL of FIG. $6B_1$, illustrating a posterior side.

FIG. $6B_3$ is an on-axis elevational view of the IOL of FIG. $6B_1$, illustrating an anterior side.

FIG. $6C_1$ is a schematic sectional view of an IOL of the invention illustrating an anterior position of an optic of the IOL.

FIG. $6C_2$ is an on-axis elevational view of the IOL of FIG. $6C_1$, illustrating a posterior side.

FIG. $6C_3$ is an on-axis elevational view of the IOL of FIG. $6C_1$, illustrating an anterior side.

FIG. 7 is a schematic view illustrating mechanical movement of a movement member of the invention.

DESCRIPTION OF THE PREFERRED EMBODIMENTS

Referring to the drawings in more detail, an intraocular lens (IOL) 10 according to an exemplary embodiment of the present invention is illustrated in FIGS. 1 and 2. Exemplary IOL 10 includes an optic 12 and a movement assembly 14 coupled to the optic 12. The optic 12, which has an optical axis O, is adapted to focus light onto a retina of an eye. The movement assembly 14 of exemplary IOL 10 cooperates with an eye to effect accommodating movement of the optic 12 and, in particular, converts radial movement (i.e., movement perpendicular to the optical axis O) of the capsular bag of an eye to axial movement (i.e., movement parallel to the optical axis O) of the optic 12.

Exemplary movement assembly 14 includes at least one movement member 16 and a suspension structure 18. Desirably, there are a plurality of movement members 16, each of which has a proximal region 20 and a distal region 22. (The terms "proximal" and "distal" are used herein with respect to the optical axis O.) The proximal region 20 is coupled to the optic 12 at a periphery 24 of the optic, and the distal region 22 is coupled to an inner periphery 26 of the suspension structure 18. The movement members 16 extend radially outwardly from the optic 12 to the suspension structure 18. As shown in FIG. 2, the suspension structure 18 has a contact surface 28 which is adapted to be in contact with a peripheral region 30 of a capsular bag 32 of an eye.

Briefly describing the anatomy of eye, the capsular bag 32 is connected to an annular ciliary muscle 34 by suspensory ligaments or zonules 36. The ciliary muscle 34 is the chief agent in accommodation, i.e., in adjusting the eye to focus on near objects. The zonules 36 retain the lens in position and are relaxed by the contraction of the ciliary muscle 34, thereby allowing a natural crystalline lens to become more convex.

Applying this anatomy to the present invention, exemplary IOL 10 is configured to facilitate movement of the optic 12 in response to the action of the ciliary muscle 34 and the zonules 36. When near vision is needed, the ciliary muscle 34 contracts, and the zonules 36 relax and reduce the equatorial diameter of the capsular bag 32, thereby moving the optic 12 anteriorly as indicated by arrow A in FIG. 1. This anterior movement of the optic 12 increases or amplifies the amount of positive (i.e., near) accommodation of the optic 12. Conversely, when the ciliary muscle 34 relaxes, the zonules 36 constrict and increase the equatorial diameter of the capsular bag 28, thereby moving the optic posteriorly as indicated by arrow P in FIG. 1. The accommodating movement principles of the present invention are discussed in detail below.

With particular reference to FIG. 2, exemplary suspension structure 18 may include a plurality of arcuate contact plates 38 respectively coupled to the movement members 16. As shown in FIG. 1, each of the contact plates 38 is configured to complement the inner peripheral region 30 of the capsular bag 32. Exemplary movement assembly 14 may include a fulcrum ring 40 coupled between each of the movement members 16, preferably at the distal regions 22 thereof, to interconnect the movement members. Defined between each of the contact plates 38 is a gap or a joint 42 for allowing the plates to move independently of each other in response to contraction and expansion of the capsular bag 32. Therefore, in accordance with the exemplary embodiment shown in the drawings, the suspension structure 18 is configured as a plurality of suspended pivotal arcuate contact plates 38 that are capable of moving responsively with the capsular bag 32.

In conjunction with the contact plates 38 of the suspension structure 18, exemplary movement members 16 of the movement assembly 14 are configured to articulate in response to contraction and expansion of the capsular bag 32. Preferably, exemplary movement members 16 are configured to convert radial movement of the arcuate plates 38 into axial movement of the optic 12. Yet more preferably, exemplary movement members 16 are configured to amplify such radial movement to provide axial movement with a magnitude greater than the radial movement. It should be noted that although a plurality of movement members 16 are shown, a single movement member having the described radial-to-axial movement amplification property is within the scope of the present invention. For example, the movement members 16 may be integrally formed (i.e., molded) as a single annular element, and thus be considered to be one piece. Alternatively, a conical coil spring or other such single member may be used with appropriate coupling structure.

More specifically, with continued reference to FIGS. 1 and 2 and with additional reference to FIG. 3, each of the movement members 16 includes a first segment 44 and a second segment 46 coupled together at a pivot 48. The distal region 22 of the first segment 44 of each movement member 16 is pivotally coupled to a respective one of the arcuate contact plates 38 at a distal pivot point 50. The proximal region 20 of the second segment 46 of each movement member 16 is flexibly or pivotally coupled to the periphery 24 of the optic 12 at a proximal pivot point 52. Accordingly, each of the movement members 16 is configured as an articulated multi-segment linkage which, as will be discussed clearly below, translates and amplifies radial movement of the contact plates 38 into axial movement of the optic 12. It should be noted that, in this respect, "articulated" has the traditional meaning of elements united by a joint or joints.

Figure 4B:
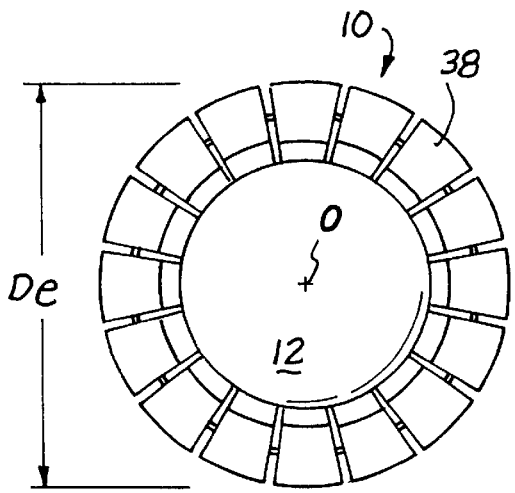
FIG. 4B is an on-axis elevational view of the IOL of FIG. 4A from a posterior side, particularly illustrating the IOL in a biased most-rearward position.
Figure 4C:
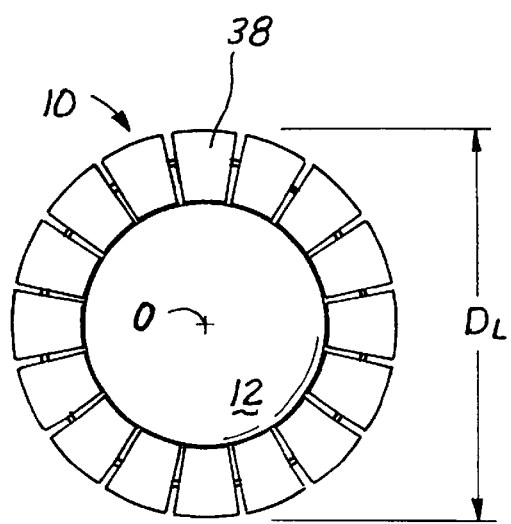
FIG. 4C is an on-axis elevational view of the IOL of FIG. 4A from an anterior side, particularly illustrating the IOL in an anterior position.
Figure 5:
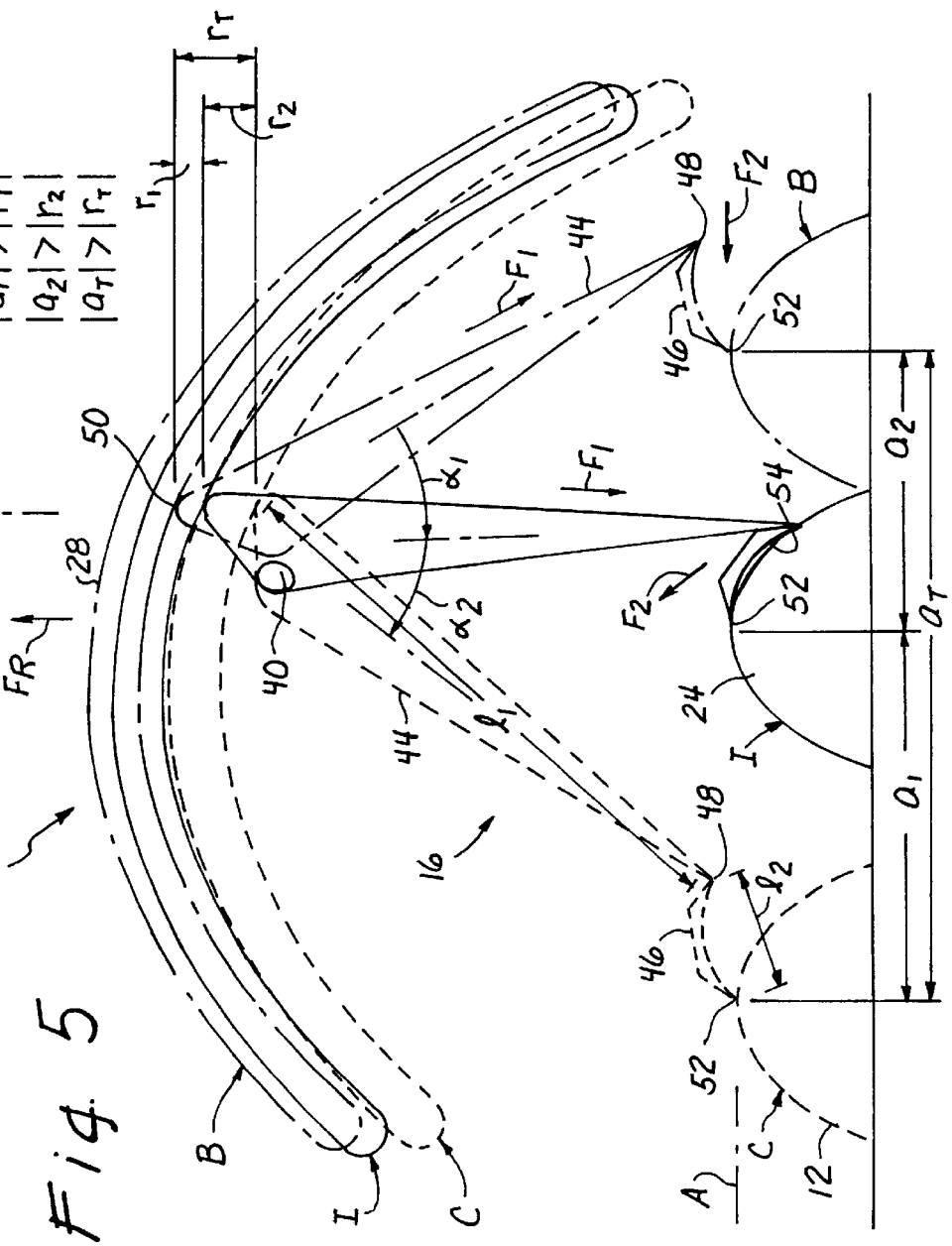
FIG. 5 is an enlarged sectional view of an IOL of the invention illustrating various positions of accommodation of an optic and corresponding movement of a movement member.

This translation and amplification feature of the IOL 10 of the present invention is illustrated in FIGS. 4, 5, and 6. Exemplary IOL 10 is shown in FIG. 4A in various states of accommodation. For example, a biased most-posterior position of the optic 10 is indicated by arrow B, shown on-axis from a posterior side in FIG. 4B, in which position the ciliary muscle 34 is relaxed in response to a need for far vision. In addition, an anterior position of the optic 12 is indicated by arrow C in FIG. 4A, shown on-axis from a posterior side in FIG. 3C, in which position the ciliary muscle 34 is contracted in response to a need for near vision. An intermediate position of the optic 12 is also shown in FIG. 4A, indicated by arrow I.

FIGS. $6B_1$ to $6B_3$ illustrate the posterior position B, namely, with respect to a fixed plane F in FIG. $6B_1$, on-axis from a posterior side in FIG. $6B_2$, and on-axis from an anterior side in FIG. $6B_3$. FIGS. $6C_1$ to $6C_3$ illustrate the anterior position C, namely, with respect to the fixed plane F in FIG. $6C_1$, on-axis from a posterior side in FIG. $6C_2$, and on-axis from an anterior side in FIG. $6C_3$.

In operation during positive accommodation, if the IOL 10 is in the biased most-rearward position B and near vision is needed, the ciliary muscle 34 contracts as indicated by arrow N in FIG. 4A. In response, the contact plates 38 move inwardly toward the optical axis O from an expanded equatorial diameter $D_e$. In doing so, with specific reference to FIG. 5, a force $F_1$ along the first segment 44 of the movement member 16 is translated into a force $F_2$ along the second segment 46 of the movement member at the pivot 48, thereby urging the optic 12 anteriorly to an intermediate position I and causing the first segment 44 to pivot anteriorly at the distal pivot point 50 through an angle $\alpha_1$. Alternatively, the IOL 10 may be oppositely configured and biased into the most-forward position (not shown) providing near vision, wherein far vision is obtained by rearward motion of the optic 12.

This translation in force amplifies the magnitude of the radial distance that the optic 12 moves. For example, and again with reference to FIG. 5, if the contact plates 38 move radially inwardly a distance $r_1$ between posterior position B and intermediate position I, then the optic 12 moves axially anteriorly a distance $a_1$ between these two positions. Accordingly to the present invention, the magnitude of axial distance $a_1$ is greater than that of radial distance $r_1$. The second segment 46 of exemplary movement member 16 may include a concave surface 54 configured to accommodate the periphery 24 of the optic 12 when in an intermediate position I during accommodation.

As the ciliary muscle 34 continues to contract, the force $F_1$ along the first segment 44 continues to be translated into the force $F_2$ along the second segment 46, thereby urging the optic 12 anteriorly from intermediate position I to anterior position C and causing the first segment 44 to pivot anteriorly at the distal pivot point 50 through an angle $\alpha_2$. If the contact plates 38 move radially inwardly a distance $r_2$ between intermediate position I and anterior position C, then the optic 12 moves axially anteriorly a distance $a_2$, the magnitude of which is greater than the magnitude of radial distance $r_2$. Accordingly, the magnitude of a total axial distance $a_T$ the optic 12 moves during accommodation (either positive or negative) is greater than a total radial distance $r_T$ that the distal pivot point 50 moves, or:

$$|a_T| > |r_T|$$

For example, the IOL 10 of the present invention may be configured so that a radial movement of the distal pivot point 50 in a magnitude of about 0.5 mm results in an axial movement of the optic 12 in a magnitude of about 2.0 mm. More generally, according to a preferred embodiment of the invention, the IOL 10 is configured so that the movement members 16 amplify radial distances r into axial distances a by at least about 100%, and preferably by about 200%.

With continued reference to FIG. 5 and additional reference to FIG. 7, the amplification in distance results in part from a relatively long first link or segment 44 of the movement member 16 indicated by $l_1$ and a relatively short second link or segment 46 of the movement member 16 indicated by $l_2$. The movement members 16 are configured such that the first and second segments 44 and 46 are angulated and converge posteriorly toward the pivot 48 when the IOL 10 is in the most-rearward position B; that is, the pivot 48 is the most posterior element of the movement member 16 when in posterior position B.

With particular reference to FIG. 7, during accommodation, the pivot 48 (i.e., a proximal end of the first segment 44 and the distal end of the second segment 46) follows a curved path Λ indicated by the dashed line. In other words, the pivot 48 moves arcuately during accommodation. When the IOL 10 is in the anterior position C, the first segment 44 is angulated anteriorly, while the second segment 46 remains in a posterior angulated orientation. Accordingly, the pivot 48 has a pivotal range that preferably does not exceed 180 degrees. In addition, it is preferable for the pivot 48 to be biased to return to its most-posterior orientation of position B.

The path Λ shown in FIG. 7 has an angular distance that is approximately equal to the product of the first length $l_1$ and the total change in angular position of the first segment 44 with respect to a radial axis R. It should be noted, however, that the path Λ is not a segment of a circumference of a perfect circle because the vertex of the angle α moves radially; accordingly, each change in arc length Δλ does not equal the exact product of the corresponding change in angle and length $l_1$.

With continued reference to FIGS. 5 and 7, the angular motion of the pivot 48 is translated to linear (i.e., axial) motion by the two-arm articulated movement member 16. More specifically, as the distal pivot point 50 (i.e., the distal end of the first segment 44) moves radially along radial axis R, the proximal pivot point 52 (i.e., the proximal end of the second segment 46) moves axially along an axial axis A. In other words, the distal end 22 of the movement member 16 (i.e., distal pivot point 50) is restricted to only radial movement (and no axial movement) along the radial axis R, and the proximal end 20 (i.e., proximal pivot point 52) is restricted to only axial movement (and no radial movement) along axial axis A. Rigid contact and engagement between the contact plates 38 and the capsular bag 32 prevents axial movement of the distal pivot point 50, and the optic 12 with a constant equatorial diameter prevents radial movement of the pivot point 52.

To accomplish negative accommodation, a restoring force $F_R$, as indicated in FIG. 5, is provided by the elastic tension of the zonules 36. The contact surfaces 28 of the contact plates 38 provide a collective large surface area subject to cellular and fibrous growth to the capsular bag 32 so that when the ciliary muscle 34 relaxes, the zonule tension draws the capsular bag and the contact plates 38 (and, accordingly, the distal pivot point 50) outwardly.

Post-operative cellular and fibrous growth of the interior of the capsular bag 32 to the contact surfaces 28 of the contact plates 38 improves functioning of the IOL 10. To further facilitate this controlled fibrosis, the contact surfaces 28 may include depressions or holes (not shown) which provide a purchase on which cells and fibrin may grow. It is anticipated that this cellular and fibrous growth may take place within the first few weeks after the IOL 10 is implanted in an eye. Accordingly, the IOL 10 is permanently attachable to the capsular bag 32. This vigorous attachment of the IOL 10 to the capsular bag 32 ensures that the optic 12 moves axially in direct response to changes in the capsular bag 32. The coupling of the contact plates 38 with the capsular bag 32 may also be accomplished with a biological glue.

Additional restoring force for facilitating negative accommodation may be provided by rearward biasing of the haptic 16. For example, a spring force may be induced and stored by the pivot 48 during positive accommodation; accordingly, when the ciliary muscle 34 relaxes, the spring force may urge the two segments 44 and 46 together. In this regard, the pivot 48 may be configured as a living hinge which is biased to return to the configuration when the IOL 10 is the posterior position B. Similarly, the connection of the first segments 44 of the haptics 16 and the contact plates 38 at the distal pivot points 50 may be configured so that a spring force is induced and stored during positive accommodation, which force is released when the ciliary muscle 34 relaxes. Those skilled in the art will appreciate that the mechanical operation of exemplary IOL 10 during negative accommodation when the ciliary muscle 34 relaxes is analogous to the foregoing description in reverse order.

Although controlled fibrosis (i.e., cellular growth) on the contact surfaces 28 of the contact plates 38 is promoted, the IOLs 10 of the invention inhibit cell growth, particularly epithelial cell growth, onto the optic 12. This is accomplished by configuring the contact plates 38 with mechanical barriers such as sharp posterior and anterior edges 56 shown in FIG. 1. The proliferation of unwanted epithelial cell growth may also be inhibited through the use of material properties.

For human implantation, exemplary IOL 10 may be configured such that the amount of positive or near accommodation is preferably at least about 1 diopter and may range up to 3.5 diopters or more. Further, exemplary IOL 10 may be configured to provide at least about 2.0 mm of axial movement anteriorly in the eye with about a reduction of about 2.0 mm in the equatorial diameter of the capsular bag 32 caused by the ciliary muscle 34 and the zonules 36.

The optic 12 may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL 10 to be rolled or folded for insertion through a small incision into the eye. Although the optic 12 as shown is a refractive lens body, the present IOLs may include a diffractive lens body, and such embodiment is included within the scope of the present invention.

The optic 12 may be either integral with or mechanically coupled to the movement assembly 14. The assembly 16 may be constructed of the same or different biocompatible materials as the optic 12, and is preferably made of polymeric materials such as polypropylene, silicone polymeric materials, acrylic polymeric materials, and the like. The movement assembly 14 is preferably deformable in much the same manner as the optic 12 to facilitate the passage of the IOL 10 through a small incision into the eye. The material or materials of construction from which the movement assembly 14 is made are chosen to provide the assembly with the desired mechanical properties, e.g., strength and deformability, to meet the needs of the particular application involved.

The IOL 10 may be inserted into the capsular bag 32 of a mammalian eye using conventional equipment and techniques, for example, after the natural crystalline lens is removed using a phacoemulsification technique. The IOL 10 is preferably rolled or folded prior to insertion into the eye to be insertable through a small incision, for example, on the order of about 3.2 mm. After insertion, the IOL 10 may be positioned in the eye as shown in FIG. 1.

If the IOL 10 is to be implanted in an adult human eye, the optic 12 preferably has a diameter in the range of about 3.5 mm to about 7 mm and, more preferably, in the range of about 5 mm to about 6 mm. Further, the IOL 10 may have an overall diameter, with the movement assembly 14 in an unstressed condition, of about 8 mm to about 11 mm or 12 mm. Additionally, the optic 12 preferably has a far-vision correction power for infinity in an un-accommodated state.

The present invention provides accommodating IOLs and methods for using such IOLs. The IOLs of the invention are configured to reduce the stretching of the capsular bag, to maintain the elasticity and/or integrity of the capsular bag, to enhance the effectiveness of the eye, particularly the function of the ciliary muscle and the zonules. The present IOLs promote the secure retention within the capsular bag by providing an enlarged contact surface to which cells and fibrin may grow. In addition, the present IOLs inhibit posterior capsule opacification (PCO).

While the present invention has been described with respect to various specific examples and embodiments, it is to be understood that the invention is not limited thereto and that it can be variously practiced within the scope of the following claims.

What is claimed is:

1. An intraocular lens comprising:
   an optic structured to focus light onto a retina of an eye and having an optical axis; and
   a movement assembly sized and structured to cooperate with the eye to effect accommodating movement of the optic and including:
      a suspension structure sized and structured to be in contact with a peripheral region of a capsular bag of the eye, the suspension structure including a plurality of arcuate contact plates; and
      a plurality of movement members coupled to the optic and to the suspension structure, each of the plurality of movement members including a first segment and a second segment, the first segment having a distal end pivotally coupled to a respective one of the contact plates at a location and a proximal end, the second segment having a distal end pivotally coupled to the proximal end of the first segment at a first pivot point and a proximal end pivotally coupled to a periphery of the optic at a second pivot point;
   wherein the movement members are sized and structured to convert and amplify radial movement of the suspension structure caused by movement of the capsular bag to axial movement of the optic, and wherein none of the movement members extend beyond a repective plane defined by a central optical axis of the optic and perpendicular to a radially extending line from the optical axis to the respective location.

2. The intraocular lens of claim 1 wherein each of the arcuate contact plates is structured to move independently in response to movement of a capsular bag of an eye.

3. The intraocular lens of claim 1 wherein the suspension structure includes a fulcrum ring pivotally coupled between the contact plates and the movement members.

4. The intraocular lens of claim 3 wherein the fulcrum ring moves axially during accommodation.

5. The intraocular lens of claim 1 wherein
   the first pivot point follows a curved path during accommodation.

6. The intraocular lens of claim 1 wherein
   the second pivot point moves axially during accommodation.

7. The intraocular lens of claim 1 wherein the movement members are biased to be in a most-rearward position.

8. The intraocular lens of claim 1 wherein the movement members are biased to be in a most-forward position.

9. The intraocular lens of claim 1 wherein each of the first segments is longer than each of the second segments.

10. The intraocular lens of claim 1 wherein the movement members are configured so that substantially radial forces along the first segment caused by a contraction of the ciliary muscle on the capsular bag are translated into substantially axial forces along the second segment.

11. The intraocular lens of claim 1 wherein the movement members are sized and structured to amplify radial movement of the suspension structure into axial movement of the optic by at least approximately 100%.

* * * * *